United States Patent [19]

Alt

[11] Patent Number: 4,688,573
[45] Date of Patent: Aug. 25, 1987

[54] TEMPERATURE DRIVEN RATE RESPONSIVE CARDIAC PACEMAKER

[75] Inventor: Eckhard Alt, Munich, Fed. Rep. of Germany

[73] Assignee: Intermedics, Inc., Angleton, Tex.

[21] Appl. No.: 747,111

[22] Filed: Jun. 20, 1985

[30] Foreign Application Priority Data

May 24, 1984 [DE] Fed. Rep. of Germany ....... 3419439

[51] Int. Cl.$^4$ .............................................. A61N 1/36
[52] U.S. Cl. ............................................... 128/419 PG
[58] Field of Search ................................. 128/419 PG

[56] References Cited

U.S. PATENT DOCUMENTS

| | | | |
|---|---|---|---|
| 3,867,950 | 2/1975 | Fischell | 128/419 PG |
| 4,428,378 | 1/1984 | Anderson et al. | 128/419 PG |
| 4,436,092 | 3/1984 | Cook et al. | 128/419 PG |
| 4,535,774 | 8/1985 | Olson | 128/419 PG |
| 4,543,954 | 10/1985 | Cook et al. | 128/419 PG |
| 4,566,456 | 1/1986 | Koning et al. | 128/419 PG |

FOREIGN PATENT DOCUMENTS 2609365  9/1977  Fed. Rep. of Germany ...... 128/419 PG

OTHER PUBLICATIONS

Wietzfeld et al "Regulation of Pacing Rate by Variations of Mixed Venous Oxygen Saturation" PACE, vol. 7, Nov–Dec. 1984, Part II, pp. 1257–1262.

Primary Examiner—William E. Kamm
Attorney, Agent, or Firm—Leitner, Greene & Christensen

[57] ABSTRACT

An exercise responsive cardiac pacemaker (1) has a stimulation electrode (3) for introduction into the atrium or ventricle of the heart, a temperature sensor (4) situated in proximity to the electrode (3) for detecting the blood temperature, and a control circuit (8, 9, 10, 11) connected to the electrode (3) and the temperature sensor (4) by which the stimulation rate of the pacemaker is adaptively adjusted depending on the blood temperature. To ensure that the cardiac pacemaker works reliably in all physiological conditions of a patient, the stimulation rate is determined with reference to a field of characteristic curves (K1, K2), the individual characteristic curves constituting distinct algorithms relating heart rate to blood temperature for different physiological conditions of the pacemaker patient. A basic characteristic curve (K2) relates distinct heart rates to absolute blood temperatures under conditions without physical stress on the pacemaker patient. A set of parallel characteristic curves (K1) relates heart rate to blood temperature under conditions of exercise, the latter curves being separated from each other by absolute temperature values along and having a slope relating heart rate rise to blood temperature rise significantly higher than the slope of the basic characteristic curve.

20 Claims, 4 Drawing Figures

TEMPERATURE DRIVEN RATE RESPONSIVE CARDIAC PACEMAKER

BACKGROUND OF THE INVENTION

1. Field of the Invention

The present invention relates generally to cardiac pacemakers, and more particularly to an exercise-responsive implantable cardiac pacemaker in which the stimulation rate is adaptively regulated according to the blood temperature of the pacemaker patient.

2. Prior Art

In situations where the natural pacemaker or pacing system of a patient's heart is disturbed because of age, disease or injury, it is customary to employ artificial pacing of the heart by implanting a cardiac pacemaker. In an atrial-triggered pacemaker, the P-wave generated preceding atrial contraction is detected to initiate the delivery of a pacing stimulus to the ventricle. It has been found that an atrial-triggered pacemaker is, to an extent, responsive to physical exertion of the patient, unlike the conventional fixed-rate pacemaker. However, in many cardiac patients, such as those suffering from atrial flutter, fibrillation, or sick-sinus syndrome, P-wave generation is not responsive to physiological conditions. Hence, the exercise-responsive advantage of atrial triggered pacemakers is not available to such patients.

In the past, many proposals have been advanced for adapting the pacemaker stimulation rate to patient exercise using a detected biological signal. Biological parameters proposed as suited for exercise-responsive adjustment of pacing rate include, for example, the pH value of the venous blood, the central venous oxygen saturation, the respiration rate, the Q-T interval (i.e., the interval from ventricular depolarization to repolarization), and the central venous blood temperature.

Cardiac pacemakers using the respiration rate or the Q-T interval for pacing rate control are currently in development and/or undergoing clinical testing. However, the use of the Q-T interval can easily cause oscillations, and thus, pacemaker-triggered tachycardia. Furthermore, the parameter these devices employ for rate control makes them particularly subject to disruption by medications currently in use to act on the electrolyte or membrane metabolism, such as beta-blocking agents, diuretics, antiarrhythmics, and digitalis.

As pointed out in publication OS 26 09 365 of the Federal Republic of Germany, dated Sept. 8, 1977, the central venous blood temperature may serve as a biological parameter for controlling or regulating the stimulation rate of a rate-adjustable cardiac pacemaker. A temperature-controlled pacemaker as described in that publication has not, to my knowledge, yet been used in actual practice. It does offer the advantage of employing a relatively Csmall and simple temperature sensor that may be incorporated in the catheter lead in proximity to the pacing electrode. The aforementioned publication proposes that the stimulation rate be adjusted in parallel with the blood temperature; that is to say, a rise in blood temperature would provide a correspondingly higher stimulation rate, not excluding a linear dependency between the two in an exemplary partial range of from 37° to 39° C.

Another rate-adaptive cardiac pacemaker similarly depending on central venous blood temperature has been proposed in U.S. Pat. No. 4,436,092, issued Mar. 13, 1984. According to that disclosure, the blood temperature is detected by a thermistor mounted on the same lead as the stimulating electrode, with the lead introduced intravenously such that the thermistor is positioned within the right ventricle of the heart. An exercise algorithm based on an observed mathematical relationship between blood temperature and heart rate in a normally functioning heart under stress, and in which constants are derived from experimental data pertaining to the particular patient who will be using the pacemaker, is utilized in conjunction with the the thermistor signal to control the pulse frequency of the pacemaker's pulse generator. This type of control appears to be similar to the general control principle proposed by Csapo et al. in the aforementioned German publication OS 26 09 365, and to the presentation by the latter at the VIII World Congress of Cardiology in Tokyo, Sept. 17-23, 1978, as detailed in the presentation manuscript. However, neither of these previously proposed approaches provides optimal adaptation of stimulation rate to the physiological condition of the cardiac pacemaker patient. In particular, the system described in the aforementioned U.S. patent employs a given relationship of blood temperature to heart rate in which heart rate is based on the summation of a base rate with a temperature dependent higher rate. Accordingly, the rate-adaptive pacemaker proposed therein provides only one single relationship between the stimulation rate and the instantaneous blood temperature.

SUMMARY OF THE INVENTION

The present invention provides a temperature-driven rateresponsive cardiac pacemaker implemented to distinguish between the physiologically determined changes of blood temperature occurring when the patient is in a resting state and those occurring when the patient is undergoing physical exertion, and to adaptively vary the stimulation rate based on change in blood temperature but according to either of two distinct and different relationships the selection of which depends on whether or not the temperature change is attributable to exercise.

My experimental data involving a multiplicity of healthy persons have led me to conclude that changes in the blood temperature and in the heart rate of the individual undergoing physical stress exhibit substantially parallel behavior, independent of the individual's short-term working capacity. Therefore, rate-responsive cardiac pacing based on the blood temperature should fulfill the following conditions:

1. a definite correlation between blood temperature and heart rate, which may be assumed to be substantially linear; and
2. an intra-individual reproducibility of this correlation, since the ratio of blood temperature to heart rate appears to a large extent to be independent of the individual's working capacity.

The blood temperature is readily and consistently measured with long-term precision using known high sensitivity temperature sensors, such as thermistors or semiconductor chip thermistors. A temperature sensor has the further advantages of being of extremely small size and low energy dissipation, making it well suited for incorporation into the lead or electrode assembly of an implantable cardiac pacemaker.

Changes in blood temperature during periods when the individual is inactive, occurring, for example, with fever, ovulation, or during the normal circadian cycle, are accompanied by changes in heart rate in normally healthy persons as well as in pacemaker patients. The correlation between changes in blood temperature and heart rate in the resting state of an individual is different from that existing when the individual is undergoing physical stress.

The present invention, in a principal aspect, recognizes the problem of differentiating between physiologically determined changes of blood temperature occurring during states of rest and physical stress of the individual; and the need to solve that problem in order to achieve adequate adaptation of the pacing rate with change of blood temperature according to which of those states is at hand. Such a solution would permit the stimulation rate to be adapted to the particular physiological condition of the pacemaker patient.

According to an important feature of the invention, the cardiac pacemaker employs means for distinguishing between a rise in the individual's blood temperature owing, say, to the normal stress of his walking up a flight of stairs and that owing to the onset of fever. More particularly, there is an evaluation of the nature of the increase (or decrease) in blood temperature over a predetermined time interval to determine its physiological origin, and a consequent selective adjustment of the pacing rate based on instantaneous blood temperature according to whether the origin lies in exercise or in the normal changes that may occur during a state of rest. According to an embodiment of the invention, this is achieved in part using a field of characterstic curves, each of which is representative of the normal dependence of heart rate on blood temperature for a specified physiological condition, storing the set of curves in a matrix memory, and controlling the stimulation rate based on blood temperature according to the correlation therebetween exhibited by the curve(s) selected in response to the determination of the attributable physiological condition.

According to a preferred embodiment of the invention, a single basic characteristic curve (hereinafter called the "basic curve") is selected as representative of the correlation between changes in absolute blood temperature and heart rate within a selected range under substantially any physiological condition in which physical stress is not a determining factor. Such a curve is representative, then, of the temperature change attributable, for example, to fever or to the normal circadian cycle. A typical example of circadian rhythm-based change is the decrease in blood temperature and heart rate accompanying sleep. While blood temperature change (increase or decrease) of about 0.5° C. occurs at night, and such change is also observed with exercise, the nightime changes occur slowly compared with the exercise changes.

The preferred embodiment further employs a set of characteristic curves which correlate changes of blood temperature and heart rate within the aforementioned selected range under conditions of physical stress (these curves hereinafter called "exercise curves." The exercise curves are individually selected for controlling the stimulation rate (in switching from control according to the basic curve) when the rate of change of blood temperature over a preset time interval exceeds a predetermined value. For example, selection of an exercise curve for pacing rate control may be based on an increase of at least 0.04° C. per minute in the patient's blood temperature.

Thus, if the cardiac pacemaker is functioning according to the basic curve, a measurement of absolute blood temperature along that curve corresponds to a distinct heart rate, and the stimulation rate of the pacemaker is controlled accordingly. For example, a heart rate of about 70 beats per minute (bpm) will typically accompany a central venous blood temperature of 37° C., while an elevated heart rate of, say, 95 bpm will accompany a fever temperature of 38.5° C. In both cases, the cardiac pacemaker patient is in a resting condition, which is identified by the absence of a time rate of change of his blood temperature in excess of the predetermined value. Hence, the stimulation rate remains under the control of the basic curve, close to the rate also observed in healthy persons.

If the patient now physically exerts himself, his blood temperature will increase per unit time at a rate significantly higher than any increase which might normally occur in the resting state during the same time interval. If that time rate of change exceeds the predetermined value (which is selected to be commensurate with any condition of exercise), the cardiac pacemaker thereupon switches functioning modes from the basic curve to the applicable exercise curve, such that the stimulation rate is regulated according to the latter curve. Since blood temperature increases with the amount of physical exercise by the individual patient, the pacing rate, controlled by temperature increase, will also increase according to the extent of exercise.

When the patient ceases the physical exertion his blood temperature will drop, which produces an adjustment of the stimulation rate of the pacemaker in the form of a decrease according to the respective exercise curve. The pacemaker continues to function in this manner until the decrease of blood temperature per unit time reaches a predetermined lower limit indicative of more gradual change or no further significant change. At that point, the reduced rate of change of blood temperature with time is indicative of the patient being in a resting state, and the pacemaker's temperature-driven rate-responsive function commences a return to the basic curve in a manner avoiding any abrupt change in the patient's heart rate.

According to another aspect of the invention, a period of time may be selected as a further criterion for predetermining the point at which the pacemaker's stimulation rate adjustment function changes from control according to an exercise curve to that of the basic curve. This period may, for example, range from a few minutes to an hour. In any case, it should be chosen to reflect a time interval following which, if no significant variation has occurred in the rate of change of the patient's blood temperature, it is appropriate to return to reliance on the basic curve for stimulation rate control. In the preferred embodiment of the invention, this period is chosen to have a duration of thirty minutes. These criteria serve to place a limit on the incidence of any pacemaker-mediated tachycardia. Of course, if the patient is actually undergoing physical stress for a longer time, there will continue to be a significant relative change in measured temperature per preselected time interval (that is, rate of change of blood temperature with time), and accordingly the adjustment of pacing rate will continue to be controlled according to the exercise curve.

If the patient is subjected to consecutive intervals of increasing and decreasing physical stress over a relatively long period, as might occur, for example, in the course of a long walk or light hike, it is possible ultimately to acieve a metabolic state of balance (i.e., equilibrium, or a steady state), where heat production equals heat loss, and in which the pacemaker follows the different metabolic conditions over a lengthy time interval with the respective adequate new rate. According to a further aspect of the invention, logic circuitry of the cardiac pacemaker is implemented to recognize the existence of such a steady-state condition, and should it continue over the entire duration of the aforementioned selected period—say, thirty minutes—to use this as a criterion for returning control of the pacing rate to the basic curve. The pacemaker circuitry is arranged to initiate a program of transition by which the pacing rate is reduced in a physiologically appropriate manner.

It follows that in the case of a long-lasting exercise, cardiac output may decrease with this reduction in stimulation rate. However, if the patient continues to undergo physical stress, with the continuing heat production his body will react with a new increase in blood temperature. This is caused by the more limited ability to dissipate the same amount of heat by maintaining the same blood skin circulation with lower heart rate, if the decrese in pacing rate leads to a lower cardiac output. Consequently, the pacemaker rate adjustment control will revert again from the basic curve to the applicable exercise curve, following this new increase in blood temperature. On the other hand, if the patient's blood temperature does not undergo significant rate of change with time after reaching the steady-state condition, the adjustment of pacing rate will continue in accordance with the basic curve.

The course (i.e., rate of change, or slope) of each of the characteristic curves may be freely selected, provided that this slope is adapted to the physiological conditions of the pacemaker patient. In particular, the curves may be linear, with the slope of the exercise curve set, for example, from 40 to 120 bpm per degree Centigrade, and the slope of the basic curve set, for example, from 5 to 25 bpm per degree Centrigrade. For most cardiac pacemaker patients, the slope is most appropriately set at or near the midpoint of these exemplary ranges, viz., 80 bpm/°C. for exercise and 15 bpm/°C. for rest. At the higher end of the blood temperature range, the curves may have a decreasing slope, which better correlates to physiological conditions.

In principle, all exercise curves may be parallel to each other, for the purpose of simplifying the internal processing of the pacemaker. In that case, the adjustment of pacing rate may be carried out with only a basic curve and the exercise curves, parallel to the abscissa, displaced according to the working point of the pacemaker.

The internal circuitry for controlling stimulation rate may be programmable as to several parameters, for the purpose of adapting the control or regulation to the particular needs of the individual patient. For example, the heart rate may be programmed for a range from 50 to 180 bpm; and the measurement range of the blood temperature may be set from 36° C. to 40° C. Also, periodic measurement (i.e., sampling) of blood temperature is preferred, and may be programmed to occur more rapidly with increasing rates of change of blood temperature per unit time. This assures rapid adjustment of stimulation rate commensurate with rapid changes of blood temperature of a patient undergoing physical stress, and thereby, to the physiological condition of the patient.

Experimental results indicate that intermittent, sudden fluctuations in the blood temperature sometimes occur, perhaps arising from the patient's respiration. In any event, the effect of a false indication of sudden change in blood temperature may be minimized by adjusting such a measurement to a median, maximum or minimum value.

To assure consistent measurement of blood temperature without regard to the patient's extremities involved in the physical exertion (that is, whether the arms, the legs, or both are involved), it is necessary that the temperature sensor be positioned at a site within the heart where good mixing of the venous blood occurs, such as at or near the boundary between the atrium and the ventricle. Preferably, the sensor is located from four to eight centimeters behind the electrode tip so that it will be properly situated whether the tip is positioned in the ventricle or (in consequence of looping of the lead) in the atrium.

Accordingly, a principal object of the present invention is to provide a cardiac pacemaker in which pacing rate is adaptive to changes in central venous blood temperature, by selectively controlling the pacing rate according to one or the other of at least two algorithms representing distinct non-constant relationships between heart rate and blood temperture.

Another object of the invention is to provide a temperature-driven rate-responsive cardiac pacemaker in which stimulation rate is adjusted according to any of a plurality of distinct curves relating stimulation rate to patient temperature in a non-constant manner, the specific curve for controlling the rate adjustment being selected according to a decision rule based on time rate of change of temperature.

A further object of the invention is to provide a method of pacing the heart rate of a cardiac patient according to distinct algorithms relating heart rate to the patient's blood temperature, in which the selection of any algorithm at a given point in time is based on rate of change of the blood temperature relative to a predetermined threshold value and on absolute blood temperature at that point in time.

BRIEF DESCRIPTION OF THE DRAWINGS

The above and other objects, aspects and advantages of the present invention will become apparent to those knowledgeable in the field to which the invention relates, from the following detailed description of a preferred embodiment of the invention, in conjunction with the accompanying drawings in which.

Figure 1:
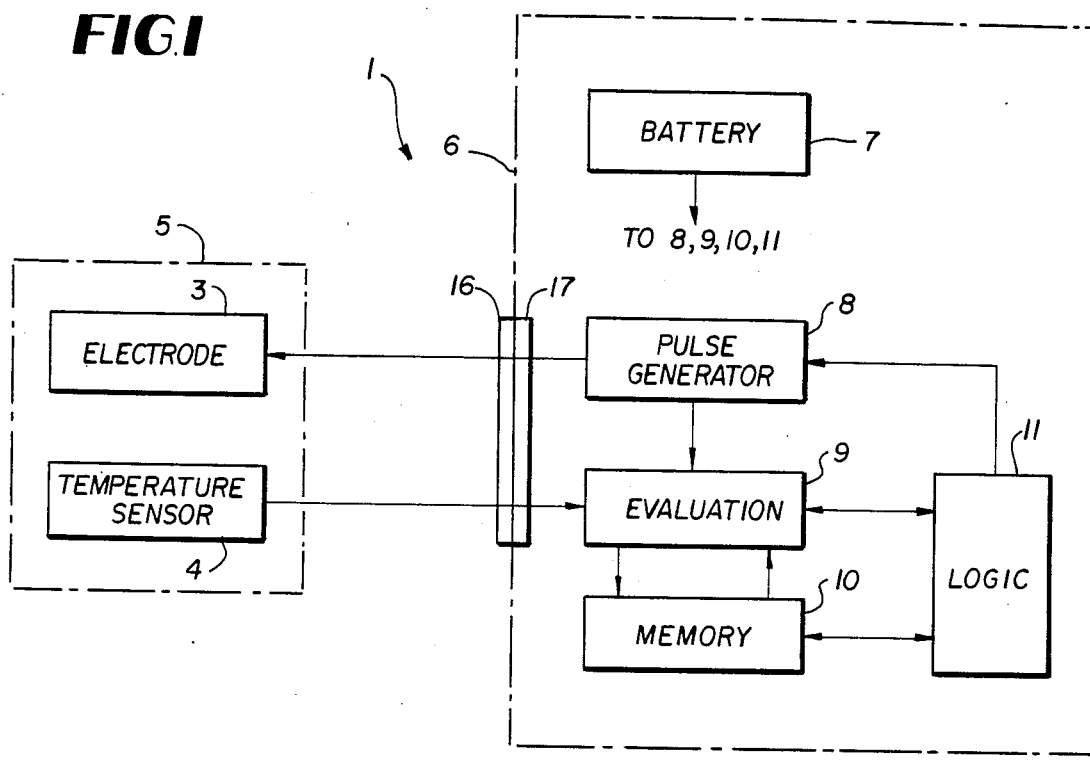
FIG. 1 is a block diagram of the preferred embodiment.

DETAILED DESCRIPTION OF THE PREFERRED EMBODIMENT:

Referring now to FIG. 1, an implantable cardiac pacemaker 1 includes a lead assembly 2 (FIG. 2) having a stimulating electrode 3 at the tip thereof. According to the invention, a high sensitivity temperature sensor 4, preferably comprising a known thermistor, chip thermistor or other tiny, highly sensitive, low dissipation thermoelectric transducer is incorporated integrally with the lead assembly and spaced about four to eight centimeters behind the electrode tip. The electrode may be positioned within either the atrium or ventricle of the patient's heart diagrammatically represented by boundary 5. The lead assembly is configured for connection with the housing (i.e., case) 6. The latter contains a battery 7 for supplying power to the entire pacemaker, pulse generator 8 for delivering pacing stimuli to the heart via electrode 3, an evaluation circuit 9, memory circuit 10, and logic circuit 11.

Figure 2:
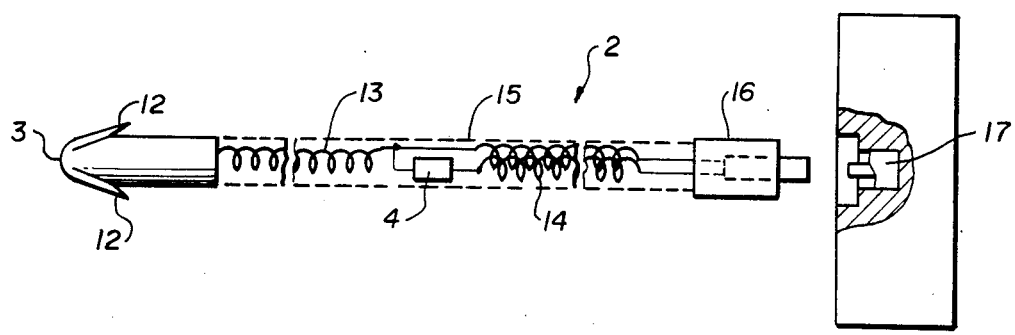
FIG. 2 is a simplified diagrammatic representation of an electrode/lead assembly arranged for unipolar stimulation and having an integral temperature sensor.

Referring now to FIG. 2, lead assembly 2 is structured for unipolar stimulation, with stimulating electrode 3 having associated therewith in proximity to its tip a set of anchoring members 12 for fixation of the electrode in proper position in the selected chamber, for example the atrium. Stimulating electrode 3 is connected to a coil 13 which may also be connected to a terminal of thermistor 4. The other terminal of thermistor 4 is connected to a second coil 14 of lead assembly 2. The coils 13 and 14 are electrically insulated from one another by suitable insulating layer 15. The lead assembly 2 is covered with a similar insulating layer 15. The lead assembly is of appropriate diameter and flexibility for conventional introduction of the electrode into the selected chamber of the patient's heart.

Coils 13 and 14 are coupled to the pacemaker circuitry within housing 6 via a male connector terminal 16 at the proximal end of lead assembly 2, which is insertable into a female connector 17 in a connector block integral with the housing. Connector terminal 16 is preferably of coaxial design and also preferably includes a reference circuit (not shown) of conventional half bridge design for calibrating the thermistor to a reference temperature. The thermistor is also connected via the reference circuit and connector 16, 17 to evaluation circuit 9.

It will be understood that other conventional connector circuits and/or configurations may alternatively be employed, the foregoing arrangement being by way of example only. This applies as well to the electrical connections to temperature sensor 4, which may for example be provided by separate insulated conductors. Moreover, the pacemaker may utilize bipolar stimulation instead of unipolar stimulation, and in that case the lead assembly 2 would include both cathode and anode at the distal end thereof.

Preferably, temperature sensor 4 has long-term stability, high sensitivity to absolute temperature and temperature change (e.g., 0.01° C.), and low energy consumption, as well as the necessary limitation on size to be accommodated in the lead assembly in the manner diagrammatically shown in FIG. 2. As noted earlier herein, such features are readily found in conventional thermistors.

Among other things, logic circuit 11 controls the interval at which the electrical signal representing the instantaneous temperature detected by sensor 4 is sampled by evaluation circuit 9 and stored in memory 10. This interval may range, for example, up to ten seconds. Evaluation circuit 9 calculates relative change between the instantaneous temperature samples and the previous samples stored in memory 10, per selected brief interval of time. Each of the evaluation circuit 9 and memory 10 is connected to logic circuit 11 by a bidirectional data bus.

The logic circuit is also connected to pulse generator 8 for the purpose of controlling the pulse repetition frequency (i.e., stimulation rate) of the generator. This control is effected through the use of characteristic curves of the type described earlier herein, and will now be further explained by way of exemplary performance of the preferred embodiment and with reference to FIG. 3. The linear curve designated K2 represents an algorithm relating heart rate to blood temperature in a non-constant manner within an exemplary temperture range from a minimum of 36° C. to a maximum of 40° C. It will be observed from FIG. 3 that over this temperature range the locus of heart rates defining curve K2 ranges from approximately 50 to approximately 120 bpm. From the earlier description, it will be recognized that curve K2 constitutes the aforementioned basic curve.

Figure 3:
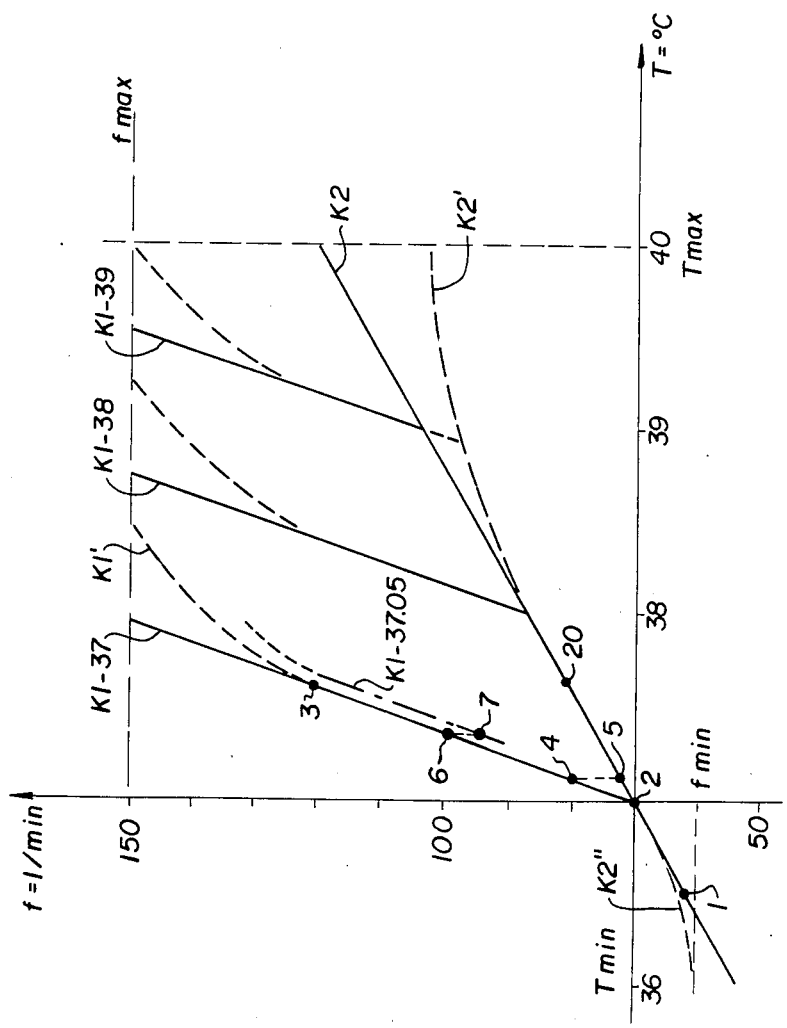
FIG. 3 is a graph of heart rate versus blood temperature for characteristic curves of the types employed in the preferred embodiment, on which a functional cycle is plotted to illustrate the mode of operation.

Superimposed on the basic curve K2 of FIG. 3 are several other linear characteristic curves designated K1-37, K1-38, and K1-39, representing at separated points of intersection with the basic curve, algorithyms distinct from that represented by the basic curve and each relating heart rate to blood temperature in a non-constant manner. It will be observed that the K1 curves are parallel to one another, with a higher slope than basic curve K2. From the previous description, it will be recognized that the K1 curves constitute the aforementioned exercise curves.

In particular, the K1 curves are developed to have, in this example, a linear variation of eighty beats per minute per degree Centigrade throughout (that is, to have a slope of 80 bpm/°C.). This is most readily observed in the case of stress curve K1-37, so designated because it intersects basic curve K2 at the 37° C. mark which happens, in this example, to be at the origin of the graph. The heart rate coinciding with that point is 70 bpm. It will further be observed that the K1-37 curve "crosses" the 150 bpm "line" along the heart rate or Y-axis, at the upper end of the graph, and that this point coincides with a temperature of 38° C. along the absolute temperature or X-axis. Inasmuch as in this example, the K1-37 curve (and each of the other exercise curves) is not only linear but, indeed, a straight line, the slope of K1-37 is 80 bpm/°C. Further, since the other exercise curves K1-38 and K1-39 are parallel to K1-37, they have the same slope.

It will be understood, however, that other slopes may be utilized for all or any portion of the exercise curves while retaining linearity and a non-constant relationship between heart rate and temperature. For example, curve K1-37 may have a region of decreasing slope with higher temperatures as indicated in the graph of FIG. 3 by dotted line K1'. In that event, the other exercise curves would have corresponding regions of decreasing slope, as indicated by the respective dotted line segments parallel to K1', each such region being representative of a more gradual variation of heart rate (or, where the relationship is used for pacing control, stimulation rate) for a given change of blood temperature as compared to the variation of heart rate along the solid line segment of each exercise curve. Similarly, basic curve K2 may have a region of decreasing slope with higher temperatures as indicated by dotted line segment K2' representing a more gradual variation of heart rate relative to blood temperature than along the solid line segment of that curve. Another region of more gradual variation of heart rate with change of temperature may be provided at the other end of basic curve K1, as indicated by dotted line segment K2'', constituting a region of increasing slope when viewed with increasing absolute temperature (e.g., from 36° C. to 37° C.). As noted above, such regions of more gradual variation of heart rate at the upper end of the absolute temperature range better correlate to normal physiological conditions.

The upper and lower limits of both the heart rate range and the absolute blood temperature range may be programmed in the cardiac pacemaker, thereby circumscribing the range within which te stimulation rate adjustment function of the pacemaker is adaptively controlled. Thus, in the exemplary graph of FIG. 3, the lower limit $f_{min}$ of the heart rate range is set at 60 bpm and the upper limit $f_{max}$ is set at 150 bpm. Similarly. for the absolute temperature range the lower limit $T_{min}$ is programmed to 36° C. and the upper limit $T_{max}$ is programmed at 40° C.

An exemplary cycle of operation of the rate adjustment control function of cardiac pacemaker 1 (FIG. 1) will now be described with reference to all of the Figures of drawing, and especialy FIG. 3. It will be assumed that the pacemaker is implanted in a patient, and as previously discussed, that the lead 2 has been introduced such that the stimulating electrode 3 is properly positioned in the desired chamber of the heart 5, with temperature sensor 4 situated in a region of strong mixing of the central venous blood (e.g., at the boundary between atrium and ventricle) in the right side of the heart. It will be understood that except for the specific components, including circuitry, employed for controlling the adjustment of the rate at which stimuli are delivered by the pulse generator, the pacemaker may be entirely of any conventional type (other than fixed rate, of course).

When the pacemaker patient is resting, and by that term is meant any state of substantial inactivity, whether reclining, sitting, standing or other position of the body, the stimulation rate of the pacemaker (that is, the pulse repetition frequency of pulse generator 8, under the control of logic circuit 11) is controlled according to the basic curve K2. For the sake of the present example of operation, it will be assumed that the patient is sleeping. Instantaneous temperature measurements (from the output waveform of sensor 4) are sampled by evaluation circuit 9 under the control of logic circuit 11, and each new sample is compared to the prior sample stored in memory 10 to determine the rate of change of blood temperature per sampling interval. In the case of a resting patient, this time rate of change of blood temperature will be less than the predetermined threshold level at which the evaluation circuit has been programmed. Hence, logic circuit 11 is responsive to this indication from the evaluation circuit to control the output pulse rate of pulse generator 8 according to the basic curve K2 stored in memory 10, that is, according to the predetermined relationship between heart rate and blood temperature of a healthy person represented by the basic curve.

Upon waking from the night's sleep, the patient's blood temperature is typically approximately 36.5° C. and his heart rate at that point is (or, as a result of the control exerted by logic circuit 11 on the stimulation rate of generator 8, is paced to be) approximately 60 bpm (point 1 on basic curve K2). With the daily rhythmic cycle constituting the individual's circadian rhythm, the patient's blood temperature ultimately rises to 37° C., and the heart rate (again, as necessary, by adaptation of stimulation rate through operation of the adjustment system) increases to 70 bpm (point 2 on basic curve K2, at the origin of the FIG. 3 graph). If the patient remains in a state of rest, his blood temperature will rise (or fall) only slightly, if at all, per unit time represented by the blood temperature sampling interval. Under these conditions, the pacemaker's internal logic circuit 11 maintains control of the pacing rate according to the stored basic curve K2. The heart rate may not remain absolutely constant with this control, and may in fact rise to a somewhat higher rate (as indicated by point 20 on the basic curve) than is strictly dictated by basic curve K2 for a blood temperature of 37° C. Nevertheless, this difference and the rise in blood temperature over time is relatively slight when the patient is not undergoing physical stress.

When the patient commences physical activity, as by walking up a flight of stairs for example, his blood temperature rises at a considerably more rapid rate than occurs in the resting case. If this rate of change of temperature as calculated by the evaluation circuit exceeds the preset threshold value (as the criterion, or decision rule based on time rate of change of temperature, that the patient is in a state of exercise, as it will with this physical stress), that determination is communicated instantaneously to the logic circuit which thereupon switches control of the pacing rate according to the applicable exercise curve K1. For example, if the decision rule for distinguishing between a resting state and an exercise state is programmed to be a time rate of change of blood temperature greater than 0.04 degree C. per minute, the determination of applicable state is made by the evaluation circuit in the selected short interval for sampling absolute blood temperature. If the blood temperature at that moment were 37° C., the shift would be from basic curve K2 to exercise curve K1-37 since the current working point of the pacemaker is at the absolute blood temperature at the intersection of those two curves.

Assume, that the blood temperature now rises to about 37.6° C. (point 3 on curve K1-37) as a consequence of the patient's physical exertion, in which event the stimulation rate is adaptively adjusted to approximately 120 bpm. When the patient ceases his physical exercise, his blood temperature will drop at a rate, perhaps rapid, that depends on his capacity for physical stress and recovery time therefrom. A somewhat rapid drop of blood temperature will be accompanied by a commensurately rapid decline in the stimulation rate according to the slope of exercise curve K1-37. The blood temperature may ultimately reach, say, 37.1° C. (point 4 on curve K137) and remain there for an extended period because of the particular patient's recovery capacity, with the stimulation rate at about 80 bpm.

In that situation, evaluation circuit 9 will determine that the time rate of change of temperature criterion is no longer met, and signal logic circuit 11 accordingly. The logic circuit will then seek to shift control of the stimulation rate back to basic curve K2. In this case, however, a gradual adjustment is implemented directly toward the point on basic curve K2 representing the patient's current blood temperature (i.e., from point 4 on curve K1-37, along the dotted line to point 5 on basic curve K2), in this example 37.1° C., where a pacing rate of about 72 bpm is generated. The reason for this operation will be explained presently. For the moment, it will suffice to observe that thereafter the stimulation rate is adjusted in correlation with measured change of blood temperature according to basic curve K2, so long as the rate of change of blood temperature is at or below the programmed threshold—which is to say so long as the patient is not subjected to further physical stress.

As previously described, it may occur that over a relatively long period with successive intervals of prolonged physical exertion, the patient's blood temperature reaches a steady state (that is, a state of balance). Assume, for the sake of example, that this condition exists at a blood temperature of 37.4° C. and a heart rate of 100 bpm (point 6 on curve K1-37), having declined to that level after rising to 37.6° C. (point 3 on that curve). Hence, the time rate of change of temperature decision rule is no longer indicative of an exercise state. Upon communicating this information to the logic circuit, control of stimulation rate will be shifted from the exercise curve directly toward the same temperature level on basic curve K2 (again with smooth transition of the stimulation rate to prevent any untoward effect on the patient as might occur with an abrupt drop in the heart rate, to be described presently in connection with FIG. 4). As described earlier, a time period may be programmed into the logic circuit—thirty minutes in the preferred embodiment—as an additional criterion which must be met to complete the determination of applicable state and of which curve is to be followed for stimulation rate control.

Assume now that the blood temperature is in a steady state condition, and there is a lapse of thirty minutes without significant change of blood temperature. This satisfies the time period criterion, which initiates a gradual transition in stimulation rate along the "line" of current temperature. In the graph of FIG. 3, this is indicated by the dotted line segment running from point 6 on exercise curve K1-37, along the 37.4° C. temperature line, to a point 7 at which the stimulation rate is 95 bpm. It will be remembered from preceding description herein that the set of exercise curves may be extensive, limited only by memory capacity and logic capability within the pacemaker's internal circuitry. In this respect, it will be understood that numerous other exercise curves K1 may be utilized in practical implementations according to the invention, relatively equally spaced from and parallel to one another. In FIG. 3, the point 7 lies along another exemplary exercise curve designated K1-137.05 which, like each of the other exercise curves, constitutes an algorithm relating stimulation rate to blood temperature in a nonconstant manner, commencing with the point of intersection of that exercise curve with the basic curve.

Should the patient continue his physical activity but suffer a reduction in cardiac output as a result of the reduced heart rate at point 7 relative to point 6, his body will compensate for the reduced output under the continuing physical stress with a corresponding rise in blood temperature. This is measured virtually instantaneously by the temperature sensor and, if the time rate of change of temperature calculated by the evaluation circuit over successive sampling intervals exceeds the present time rate criterion (as it would under these conditions), results in an interruption of the return toward control of stimulation rate according to the basic curve K2. Instead, the heart rate will either be returned to the higher rate at point 6 on exercise curve K1-37 and thence along that curve, or if point 7 is then on or in closer proximity to another exercise curve above it stimulation rate level, will proceed to and commensurately along that other curve. In this example, since point 7 lies on exercise curve K1-37.05 which is stored in the pacemaker memory or otherwise programmed in the logic circuit, the control of adjustment of the stimulation rate will follow that stress curve—at least until such time as the criteria for that mode of operation are no longer met.

Such adjustment, along the K1-37.05 curve in this example, is physiologically appropriate because it represents the proper regulation of stimulation rate for the patient's physiological state, blood temperature, and physical capacity. If the physical stress were then to subside, of course, the pacing rate adjustment would continue under control of that exercise curve with decrease in blood temperature, until the exercise and/or time period criteria are no longer satisfied. At that time, the logic control will undergo smooth transition in pacing rate at the then-current blood temperature toward the basic curve, for ultimate control according to the latter unless a preestablished criterion is again satisfied as described above.

Figure 4:
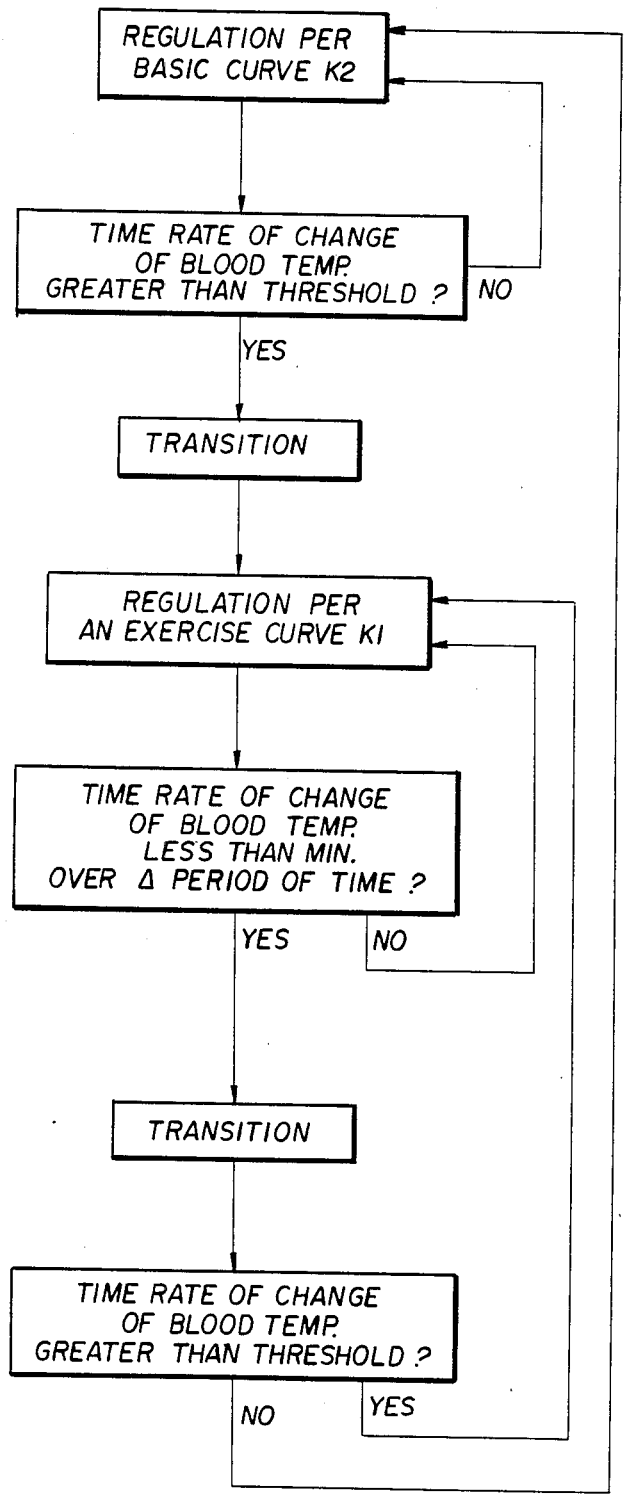
FIG. 4 is a flow diagram useful in explaining the function of transitioning between pacing rate adjustment curves in the preferred embodiment.

The flow diagram of FIG. 4 is useful to explain the smooth transitioning of stimulation rate adjustment from the basic curve to an exercise curve, or from one exercise curve to another, or from an exercise curve to the basic curve, according to an internal program routine of the adjustment system and over a programmable time interval. Assume, for example, that the stimulation rate is being regulated according to the basic curve K2 (represented by the top block in FIG. 4). The other blocks of that Figure represent stress curves, criteria, or programmed functions according to their respective designations. Assume further that the exercise criterion is m, so that a time rate of change of blood temperature exceeding m is determined (by evaluation circuit 9) to be indicative of an exercise state. As previously noted, in the preferred embodiment m is 0.04° C./min. Then a time rate of change of blood temperature less than a predetermined threshold just exceeding m, depending on the sensitivity of the temperature sensor and the evaluation circuit, will encompass m and everything below that value, and therefore represent the criterion or decision rule, as a function of time rate of change of temperature, for determining the change from a resting state to an exercise state (or vice versa), and thus for selection of the proper exercise or rest algorithm. In FIG. 4, this immediately higher value is designated n. As before, a time period is utilized as another criterion, useful for both controlling stimulation rate under a steady state condition of blood temperature and for limiting incidence of pacemaker-triggered tachycardia.

Now suppose the patient's blood temperature begins to rise, for whatever reason. The change of blood temperature $\Delta T$ over the sampling time interval $\Delta t$, or $\Delta T/\Delta t$, is compared to m. If this exercise criterion is not met, that is, the time rate of change of blood temperature does not exceed m, control of stimulation rate remains in accordance with the basic curve K2 inasmuch as the determination is that the patient remains in a resting state, notwithstanding the detected rise in blood temperature.

On the other hand, if the comparison demonstrates that $\Delta T/\Delta t > m$, the regulation of stimulation rate is shifted to the appropriate exercise curve K1 according to a programmed transition function. Further comparisons are made as the adjustment of pacing rate is controlled according to the entry exercise curve, to determine whether the rate of change of blood temperature with time is less than n, and if so, whether that situation prevails for the preset period of time—30 minutes, in the preferred embodiment. If this criterion is met, the regulation of pacing rate undergoes a programmed transition in stimulation rate toward return of control to basic curve K2. If that criterion is not met, control remains with the entry exercise curve.

During the transitional return toward control according to basic curve K1 at the applicable blood temperature, the exercise criterion is continually re-examined at the temperature sampling interval. If that criterion is met, control is returned to the exercise curve K1 in closest proximity (and in the appropriate direction relative to temperature) to the then-current working point of the pacemaker. If the exercise criterion is not met, the control of pacing rate returns to the basic curve K2.

Although a specific preferred embodiment of the invention has been described herein, variations of that embodiment will become readily apparent to those skilled in the field to which the invention pertains from a reading of the foregoing description, without departing from the concepts of the invention. Accordingly, it is intended that the present invention be limited only by the appended claims.

I claim:

1. An implantable cardiac pacemaker for adaptively varying the heart rate of a patient according to whether the patient is resting or undergoing exercise, comprising
    sensing means for measuring the blood temperature of the patient and for generating an electrical signal respresentative of that instantaneous temperature,
    means responsive to the temperature-representative signal for determining whether the time rate of change of the blood temperature is indicative of a state of rest or exercise by the patient,
    means storing separate mathematical relationships between heart rate and blood temperature having, respectively, a rate of change in the range from 5 to 25 beats per minute per degree C. representing rest state of the patient, and a rate of change in the range from 40 to 120 beats per minute per degree C. representing exercise state of the patient, and
    means responsive to the state-determining means for stimulating the patient's heart rate according to one of the stored rest state and exercise state relationships between heart rate and blood temperature selected based on whether said determination is that the patient is then in the rest state or the exercise state.

2. The cardiac pacemaker of claim 1, in which said determining means includes means for periodically sampling the temperature-representative signal, and means for comparing the present sample of said signal with past samples thereof for the determination of time rate of change of blood temperature as indicative of rest state or exercise state.

3. The cardiac pacemaker of claim 1, in which said stimulating means includes means for producing a smooth transition between the pacing rates at which the patient's heart is stimulated in the rest and exercise states.2

4. The cardiac pacemaker of claim 3, in which said stimulating means further includes programmable means for preselecting a value for minimum relative change in blood temperature over a specified period of time, and
    said means for producing a smooth transition includes means for shifting the control of stimulation from said exercise state relationship to said rest state relationship in response to a relative change of the blood temperature measured by said sensing means which is less than said preselected value over the specified period of time.

5. A cardiac pacemaker for delivering electrical stimuli to a patient's heart, comprising
    means for generating electrical stimuli at a periodic rate,
    means for producing a signal representing temperature of the patient's central venous blood at a given point in time,
    means responsive to said signal over time for determining from the rate of change of the patient's blood temperature over a predetermined interval of time whether the patient is then in a state of exercise or a state of non-exercise,
    means providing a first continuous function relating stimulation rate to measured blood temperature for a non-exercise state and providing a second continuous function relating a faster rate of change of stimulation rate to a measured unit of blood temperature for an exercise state than that of said first continuous function, and
    means responsive to said determination for regulating the rate at which said electrical stimuli are generated by said generating means according to both the instantaneous measurement of the patient's blood temperature and the determined state of the patient, commensurate with said first continuous function when the patient is determined to be in a non-exercise state and commensurate with said second continuous function when the patient is determined to be in an exercise state.

6. The pacemaker of claim 5, in which
    said rate regulating means includes means for producing a gradual transition between the rates at which said electrical stimuli are generated when the patient goes from a non-exercise state to an exercise state and vice versa.

7. The pacemaker of claim 6, in which said means for producing a gradual transition includes
    means for establishing a predetermined value representing minimum change of blood temperature over a specified period of time, and
    means for smoothly returning the rate at which electrical stimuli are generated under regulation by said second continuous function to a rate regulated by said first continuous function upon a measured change of blood temperature which is less than said predetermined value over said specified period of time.

8. A stimulus generator for a stimulation rate-adaptive cardiac pacemaker, comprising
    means for detecting a physiological parameter in a pacemaker patient representative of either a state of patient rest or a state of patient exercise, depending on the time rate of change of the parameter,
    means storing two different algorithms relating heart rate to said parameter, one for rest state and the other for exercise state, in which the exercise state algorithm specifies a greater rate of change of heart rate than that specified by said rest state algorithm relative to a unit change of said parameter,
    means for implementing a decision rule based on time rate of change of said parameter, by which a decision is to be made for selecting between said two different algorithms, means for controllably generating electrical stimuli at a variable rate, and means responsive to detection of said parameter to apply said decision rule to select between the two algorithms, for controlling the rate at which stimuli are generated by said controllable generating means according to the selected algorithm, and thereby, according to a heart rate physiologically appropriate to the patient's state.

9. The stimulus generator according to claim 8, wherein said detecting means comprises means for detecting central venous blood temperature of the patient.

10. A method for pacing the heart rate of a cardiac patient, comprising measuring the patient's absolute blood temperature at successive points in time, relating desired pacing rate to blood temperature according to an algorithm characterizing a metabolic state of the patient representing physical inactivity, and also according to an algorithm characterizing a metabolic state of the patient representing physical activity, the two algorithms differing in rate of change of pacing rate relative to unit change of blood temperature, pacing the patient's heart at a selectively variable rate, selecting one of the algorithms at any of said points in time based on the rate of change of the measured blood temperature with time relative to a predetermined threshold value, the activity algorithm being selected when said rate of change exceeds said threshold value and the inactivity algorithm being selected when said rate of change is less than said threshold value, and adjusting the pacing rate under the control of the selected algorithm.

11. In a cardiac pacemaker having control means for automatic adaptation of the periodic stimulation rate generated by the pulse generator of the pacemaker to the metabolic state of the pacemaker patient, in which said control means includes temperature sensor means, a pacing lead with a stimulation electrode connected to said pulse generator, said sensor means situated in said pacing lead in proximity to said electrode for transvenous introduction with said electrode into the atrium or ventricle of the patient's heart for detecting the instantaneous tempeature value of venous blood therein at any given point in time, and circuit means connected to said sensor means and to said pulse generator for adjusting said stimulation rate based on the blood temperature detected by said sensor means, the improvement in which said circuit means comprises means for storing a basic mathematical curve defining a predetermined relationship between heart rates and instantaneous blood temperature values corresponding to non-exercise conditions for a human being, and plural exercise mathematical curves commencing from diverse instantaneous blood temperature values along said basic curve and each defining a predetermined relationship between heart rates and relative change of blood temperature corresponding to exercise conditions for a human being, means coupled to said pulse generator for selectively applying one of said basic mathematical and plural exercise mathematical curves to adjust said stimulation rate according to the selectively applied curve, means for preselecting a desired threshold value of the relative change of the increasing blood temperature, and means coupled to said applying means and responsive to the instantaneous blood temperature values detected by said sensor means and to the relative change thereof over time for selecting said basic curve for application to adjust said stimulation rate whenever the relative change of the increasing blood temperature is less than said preselected threshold value, and for selecting an exercise curve for application to adjust said stimulation rate once the relative change of the increasing blood temperature exceeds said threshold value, said selecting means including means for designating a particular exercise curve according to the instantaneous blood temperature value detected by said sensor means at the point in time that the relative change of the blood temperature exceeds said threshold value.

12. The invention according to claim 11, wherein said exercise curves and said basic curve stored by said storing means are continuous functions of their respective parameters; and the slope, relating heart rate to relative change of blood temperature, of each exercise curve is greater than the slope, relating heart rate to instantaneous blood temperature value, of said basic curve, such that when an exercise curve is selectively applied to adjust stimulation rate the stimulation rate undergoes a more rapid change for a given unit change of the detected blood temperature than when the basic curve is selectively applied to adjust stimulation rate.

13. The invention according to claim 12, wherein the slope of each of said exercise curves is in the range between 40 and 120 beats per minute per degree C. and the slope of said basic curve is in the range between 5 and 25 beats per minute per degree C.

14. The invention according to claim 12, wherein the slope of each exercise curve and of the basic curve diminishes in the range of the higher instantaneous blood temperature values for that respective curve.

15. The invention according to claim 11, wherein said selecting means further includes programming means for preselecting a desired minimum relative change of blood temperature over a specified period of time, and means for effecting a smooth transition from adjustment of said stimulation rate according to a selected exercise curve, toward selection and subsequent adjustment of said stimulation rate according to said basic curve, in response to a relative change of blood temperature less than the preselected relative change, to provide a gradual change in rate during said transition, whereby the selecting means thereafter selects said basic curve for application to adjust the stimulation rate unless and until the relative change of the increasing blood temperature once again exceeds said threshold value.

16. The invention according to claim 15, wherein said preselected threshold value is +0.04 degree C. per minute.

17. The invention according to claim 11, wherein said selecting means further includes means for storing instantaneous blood temperature values detected by said sensor means at preselected points in time, from which relative changes of detected blood temperature over time are obtainable for comparison with said threshold value, said instantaneous blood temperature values detected by said sensor means at preselected points in time constituting a moving functional working point of stimulation rate for successive detected instantaneous blood temperature values along the respective selected curve.

18. The invention according to claim 11, wherein said selecting means further includes means for periodically scanning the instantaneous blood temperature values detected by said sensor means at a predetermined rate which is varied proportionally with increase or decrease of the detected blood temperature.

19. The invention according to claim 11, wherein said sensor means is situated at a distance of from 4 to 8 centimeters from said stimulation electrode in said pacing lead.

20. The invention according to claim 11, wherein the improvement further comprises means connected to said sensor means for calibration thereof to detect absolute instantaneous temperature values.

* * * * *

UNITED STATES PATENT AND TRADEMARK OFFICE
CERTIFICATE OF CORRECTION

PATENT NO. : 4,688,573
DATED : August 25, 1987
INVENTOR(S) : Eckhard Alt

It is certified that error appears in the above-identified patent and that said Letters Patent is hereby corrected as shown below:

Col. 1, line 56, delete "Csmall" and insert --small--.

Col. 2, line 32, delete "rateresponsive" and insert --rate responsive--.

Col. 8, line 23, delete "algorithyms" and insert --algorithms--.

Col. 9, line 2, delete "K1" and insert --K2--;

line 12, delete "te" and insert --the--;

Col. 10, line 53, delete "K137" and insert --K1-37--.

Col. 11, line 47, delete "K1-137.05" and insert --K1-37.05--;

line 68, delete "it" and insert --its--.

Col. 13, line 61 (Claim 3), delete "2".

Signed and Sealed this

Twenty-second Day of March, 1988

Attest:

DONALD J. QUIGG

Attesting Officer

Commissioner of Patents and Trademarks